(12) United States Patent
Salaet Ferre et al.

(10) Patent No.: US 9,321,726 B2
(45) Date of Patent: Apr. 26, 2016

(54) PROCESS FOR PREPARING ROFLUMILAST

(71) Applicant: INTERQUIM, S.A., Sant Cugat del Vallés—Barcelona (ES)

(72) Inventors: Josep Salaet Ferre, Sant Cugat del Vallés—Barcelona (ES); Francisco Marquillas Olondriz, Sant Cugat del Vallés—Barcelona (ES)

(73) Assignee: Interquim, S.A., Barcelona (ES)

( * ) Notice: Subject to any disclaimer, the term of this patent is extended or adjusted under 35 U.S.C. 154(b) by 0 days.

(21) Appl. No.: 14/426,881

(22) PCT Filed: Oct. 16, 2013

(86) PCT No.: PCT/EP2013/071607
§ 371 (c)(1),
(2) Date: Mar. 9, 2015

(87) PCT Pub. No.: WO2014/060464
PCT Pub. Date: Apr. 24, 2014

(65) Prior Publication Data
US 2015/0246884 A1 Sep. 3, 2015

Related U.S. Application Data

(60) Provisional application No. 61/738,028, filed on Dec. 17, 2012.

(30) Foreign Application Priority Data

Oct. 17, 2012 (ES) .................................. 201231598

(51) Int. Cl.
| | | |
|---|---|---|
| *C07D 213/75* | (2006.01) |
| *C07D 233/60* | (2006.01) |
| *C07D 249/08* | (2006.01) |
| *C07D 207/408* | (2006.01) |
| *C07D 209/48* | (2006.01) |
| *C07D 295/104* | (2006.01) |
| *C07D 233/90* | (2006.01) |
| *C07D 249/10* | (2006.01) |

(52) U.S. Cl.
CPC .......... *C07D 213/75* (2013.01); *C07D 207/408* (2013.01); *C07D 209/48* (2013.01); *C07D 233/60* (2013.01); *C07D 233/90* (2013.01); *C07D 249/08* (2013.01); *C07D 249/10* (2013.01); *C07D 295/104* (2013.01)

(58) Field of Classification Search
None
See application file for complete search history.

(56) References Cited

FOREIGN PATENT DOCUMENTS

CN 102617339 A * 8/2012

OTHER PUBLICATIONS

International Search Report for PCT/EP2013/071607 mailed Dec. 11, 2013.*
Han S-Y et al, "Recent development of peptide coupling reagents in organic synthesis", Tetrahedron, vol. 60, No. 11, Mar. 8, 2004, pp. 2447-2467.*

* cited by examiner

*Primary Examiner* — Zinna Northington Davis
(74) *Attorney, Agent, or Firm* — Birch, Stewart, Kolasch & Birch, LLP

(57) ABSTRACT

The invention relates to a process for the preparation of Roflumilast by reaction of an activated form of 3-(cyclopropylmethoxy)-4-(difluoromethoxy)-benzoic acid with an activating agent selected from (a) carbonyldiimidazole (CDI), (b) 1,1'-carbonyl-di-(1,2,4-triazol) (CDT), (c) 1,1'-carbonyl-bis-(2-methylimidazol), (d), 1'-carbonyl-dipyperidin, (e) N,N'-dicyclohexylcarbodiimide (DCC), (f) N,N'-diisopropylcarbodiimide (DIC), (g) 1-ethyl-3-(3-dimethylaminopropyl) carbodiimide (EDC) and a combination of one of the previous (a)-(g) with (h) N-hydroxysuccinimide or (i) N-hydroxyphthalimide, and the subsequent reaction with 3,5-dichloropyridine-4-amine in the presence of an inorganic base. The invention also relates to the synthesis intermediates.

20 Claims, 1 Drawing Sheet

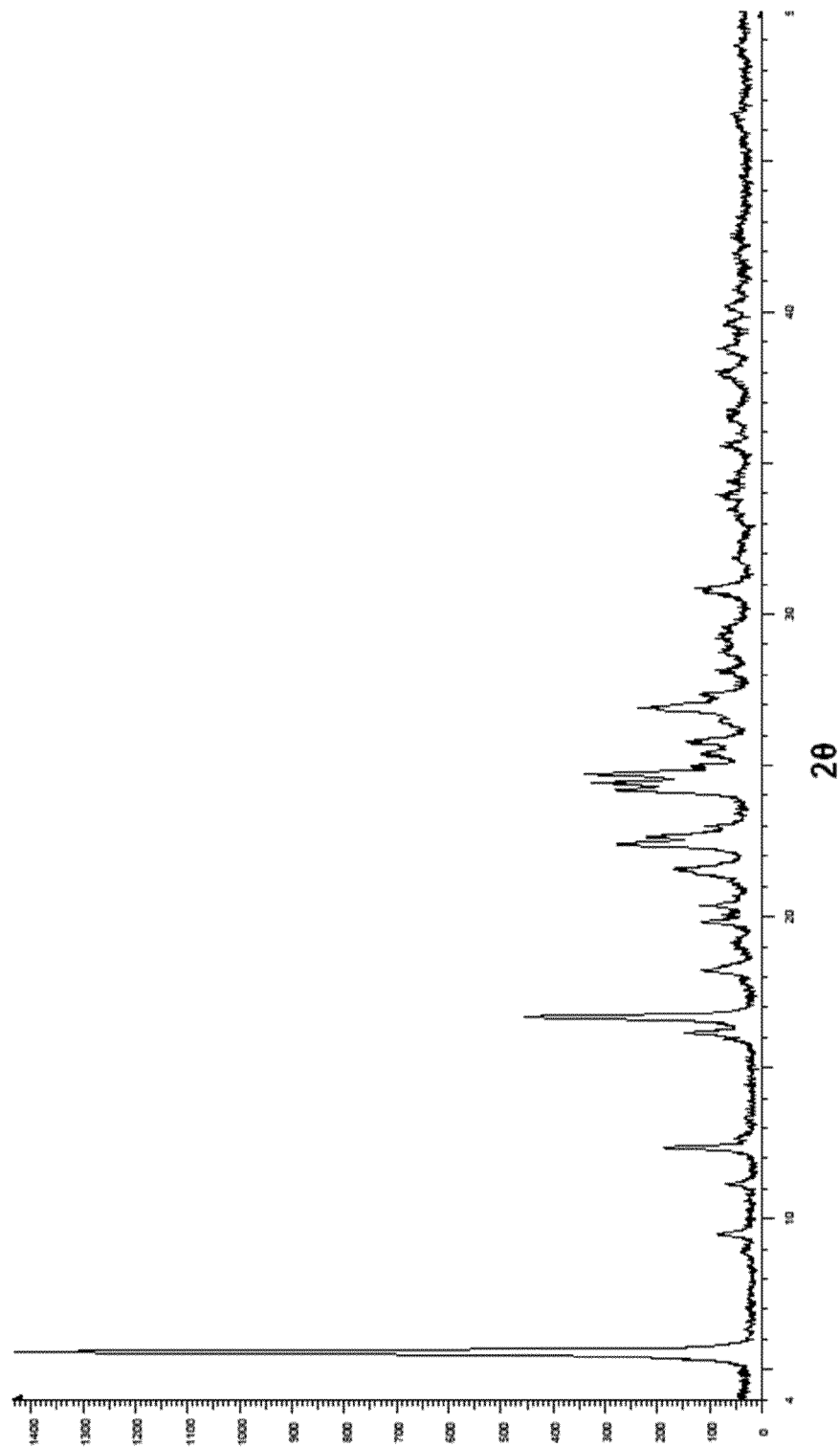

PROCESS FOR PREPARING ROFLUMILAST

CROSS REFERENCE TO RELATED APPLICATIONS

This application is the National Phase of PCT International Application No. PCT/EP2013/071607, filed on Oct. 16, 2013, which claims priority under 35 U.S.C. 119(e) to U.S. Provisional Application No. 61/738,028, filed on Dec. 17, 2012, and under 35 U.S.C. 119(a) to Patent Application No. P201231598, filed in Spain on Oct. 17, 2012, all of which are hereby expressly incorporated by reference into the present application.

FIELD OF THE INVENTION

The present invention is comprised within the procedures for obtaining Roflumilast, a phosphodiesterase IV inhibitor compound.

PRIOR STATE OF THE ART

Roflumilast compound is a phosphodiesterase IV inhibitor compound, of clinical application as antiallergic and antiasthmatic. It corresponds chemically to 3-(cyclopropylmethoxy)-N-(3,5-dichloropyridine-4-yl)-4-(difluoromethoxy)-benzamide and its structural formula is:

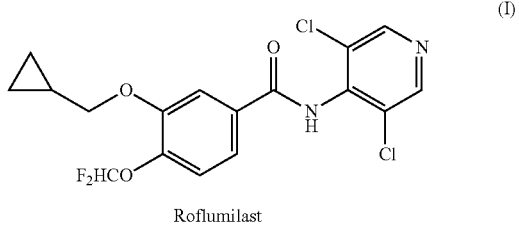 [SMILES: O=C(Nc1c(Cl)cncc1Cl)c1ccc(OC(F)F)c(OCC2CC2)c1]

Roflumilast

The preparation of roflumilast (I) has been described in the following patent documents: WO9501338, WO2004033430, WO2004080967, WO2005026095 and IN478/MUM/2004.

In WO9501338 the reaction of 3-(cyclopropylmethoxy)-4-hydroxy-benzaldehyde with chlorodifluoromethane in the presence of sodium hydroxide and benzyl-trimethylammonium chloride (BTMA) in dioxane/water leads to 3-(cyclopropylmethoxy)-4-(difluoromethoxy)-benzaldehyde, which by oxidation with sodium chlorite and sulphamic acid yields 3-(cyclopropylmethoxy)-4-(difluoromethoxy)-benzoic acid. Chlorination of this acid with thionyl chloride in reflux toluene provides the corresponding acyl chloride, which is finally condensed with 3,5-dichloropyridine-4-amine in the presence of sodium hydride in tetrahydrofuran to thus reach roflumilast (I). These procedures are set out in Scheme 1.

Scheme 1

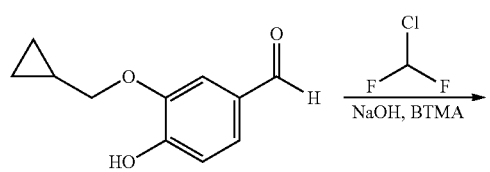

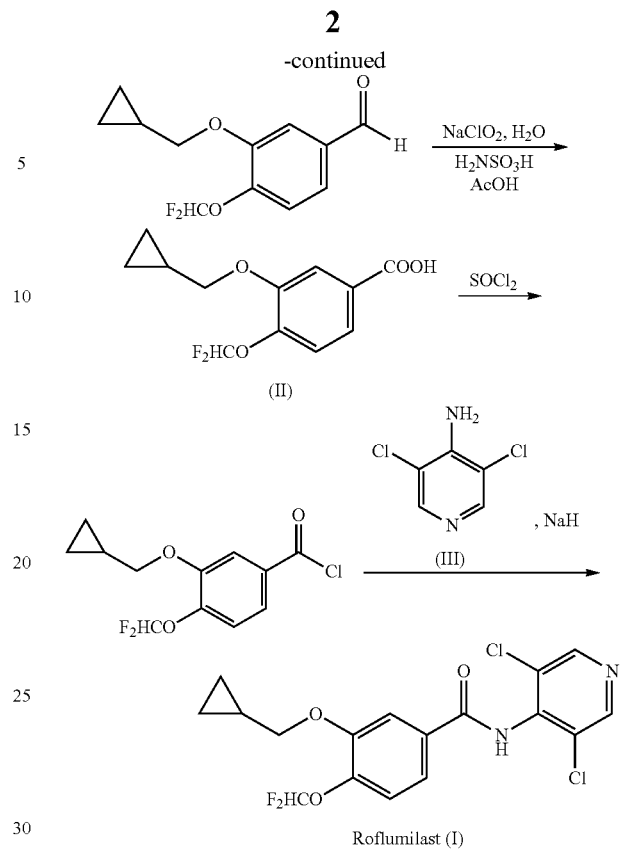

The process claimed in WO2004080967 is based on the reaction of an activated derivative of 3-(cyclopropylmethoxy)-4-difluoromethoxy-3-methoxybenzoic acid (preferably acyl chloride) and an alkaline salt of 3,5-dichloropyridine-4-amine (preferably potassium salt) characterised in that the molar ratio of alkaline salt of 3,5-dichloropyridine-4-amine and the activated derivative is 1.5-3, preferably 1.8-2.7. The reaction is performed preferably in tert-BuOK and dimethylformamide or N-methylpyrrolidone.

WO2005026095 describes a process where alkylation of 3,4-dihydroxy-benzoate methyl with bromomethyl cyclopropane in the presence of potassium carbonate in acetone leads to methyl 3-(cyclopropylmethoxy)-4-hydroxy-benzoate, which by reaction with chlorodifluoromethane in the presence of sodium hydroxide and tetrabutylammonium bromide in toluene/water yields 3-(cyclopropylmethoxy)-4-(difluoromethoxy)-methyl benzoate. Hydrolysis of the methyl ester group with sodium hydroxide in water provides the corresponding 3-(cyclopropylmethoxy)-4-(difluoromethoxy)-benzoic acid. The latter, by treatment with thionyl chloride in the presence of catalytic dimethylformamide at 90° C., provides the corresponding acid chloride. The reaction of acid chloride with 3,5-dichloropyridine-4-amine in the presence of sodium hydride in tetrahydrofuran leads to roflumilast (I). These procedures are set out in Scheme 2.

Scheme 2

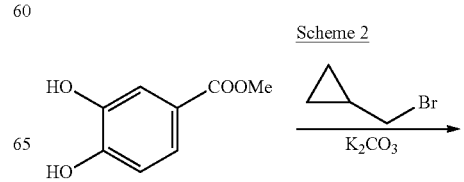

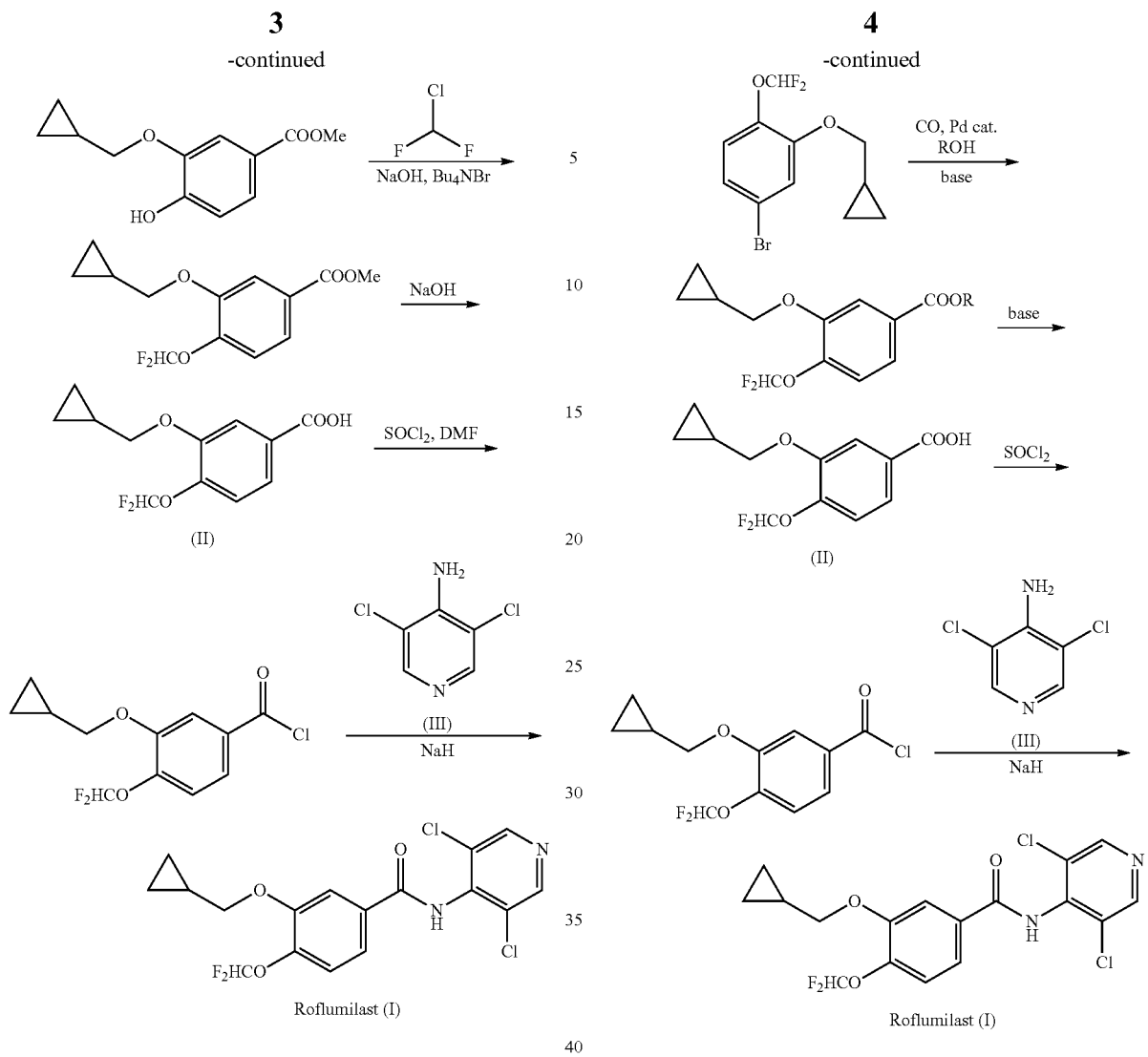

WO2004033430 describes the preparation of Roflumilast (I) according to Scheme 3.

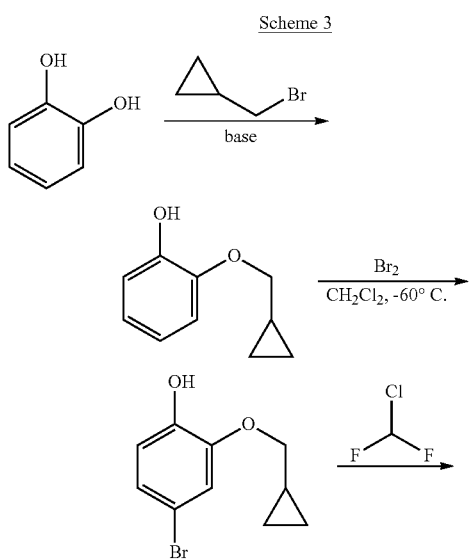

IN478/MUM/2004 describes the preparation of Roflumilast (I) by treatment of 3,4-dihydroxybenzaldehyde with excess alkaline salt of formula YCF$_2$COOA, where Y is halogen and A is an alkaline metal, in wet sulfolane, followed by reaction of 4-(difluoromethoxy)-3-hydroxy-benzaldehyde thus formed with bromomethyl cyclopropane in the presence of potassium carbonate in dimethylformamide. The 3-(cyclopropylmethoxy)-4-(difluoromethoxy)-benzaldehyde obtained is then subject to oxidation with sodium chlorite in an acid medium. The resulting 3-(cyclopropylmethoxy)-4-(difluoromethoxy)-benzoic acid is made to react with thionyl chloride to form the corresponding acid chloride, which subsequently is made to react with 3,5-dichloropyridine-4-amine in the presence of sodium hydride in tetrahydrofuran to reach Roflumilast (I). These procedures are set out in Scheme 4.

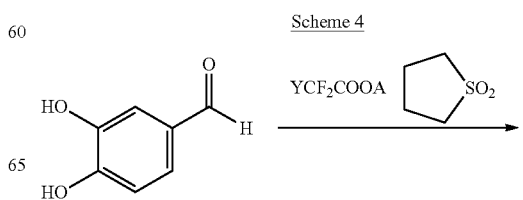

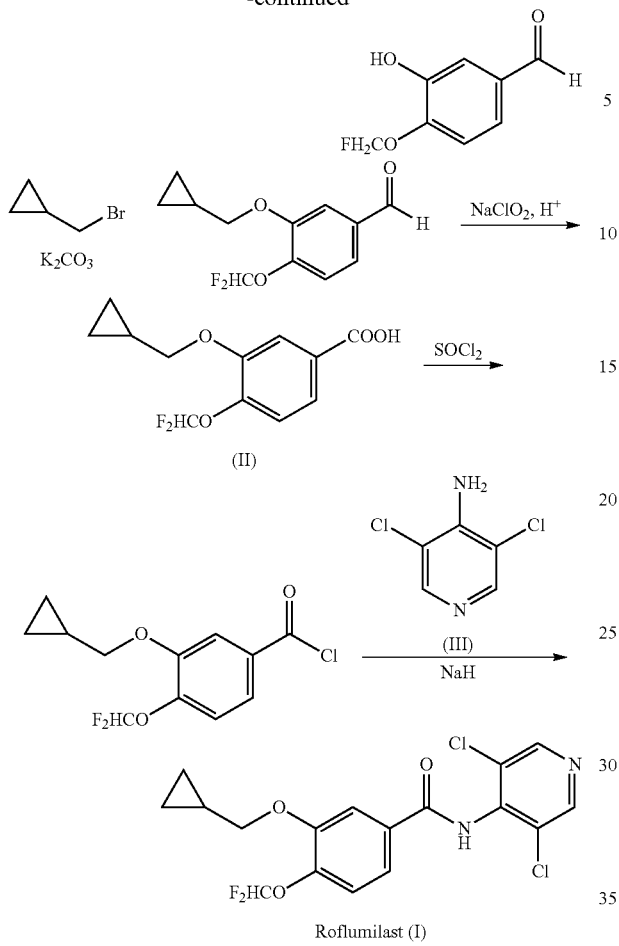

Roflumilast (I)

Finally, variation of the above procedures have been submitted in CN102276522 CAPLUS 2011:1626719, CN102336703 CAPLUS 2012:170113, CN102336704 CAPLUS 2012:170199, CN102336705 CAPLUS 2012:170217 and CN102351787 CAPLUS 2012:242538.

In summary, the routes known to date involve the use of very strong bases, as in the case of sodium hydride or tert-BuOK, that are not advisable in industrial processes due to the danger involved in handling them. Another disadvantage of the procedures of the previous state of the art is the formation of the intermediate 3-(cyclopropylmethoxy)-4-(difluoromethoxy)benzoyl chloride (II); for its structure, this intermediate is considered to involve a potential risk of genotoxicity, which would lead to limiting its contents in the final product according to the regulations for this type of compounds. In addition, thionyl chloride, a toxic reagent, is used in the formation of this intermediate. Finally, WO2004080967 highlights the need to use large excesses of 3,5-dichloropyridine-4-amine, which represents an economic and environmental drawback.

Therefore, according to the procedures described to date, it is concluded that a new procedure should be available for obtaining industrially Roflumilast (I) that uses more acceptable bases on an industrial basis, avoids the formation of intermediates and the use of reagents that may be toxic, and limits the excesses of 3,5-dichloropyridine-4-amine.

BRIEF DESCRIPTION OF THE INVENTION

This invention provides a new, advantageous procedure for obtaining Roflumilast (I), that can be implemented industrially, that uses activated forms of acid other than acid chloride, which is considered due to its structure as being a compound with genotoxic activity, thus avoiding also the use of thionyl chloride, a toxic, corrosive agent, in the preparation of these activated forms. As an additional advantage, the procedure of the present invention allows obtaining Roflumilast with yields higher than 80%.

Therefore, in a first embodiment this invention is aimed at a process for the preparation of a compound of formula (IV):

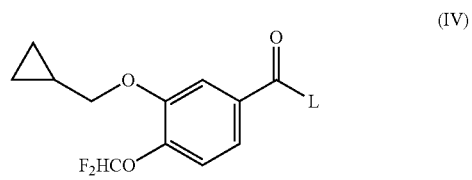

where L is (a) 1H-imidazol-1-yl, (b) 1H-1,2,4-triazol-1-yl, (c) 2-methyl-1H-imidazol-1-yl, (d) piperidin-1-yl, (e) N,N'-dicyclohexylcarbamimidoyloxy, (f) N,N'-diisopropylcarbamimidoyloxy, (g) N'-(3-(dimethylamino)propyl)-N-ethylcarbamimidoyloxy, (h) 2,5-dioxopyrrolidin-1-yloxy, or (i) 1,3-dioxoisoindolin-2-yloxy, comprising:
i) activation of a compound of formula (II):

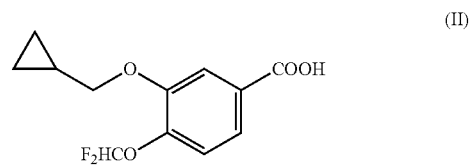

with an activating agent selected, respectively, from (a) carbonyldiimidazole (CD), (b) 1,1'-carbonyl-di-(1,2,4-triazol) (CDT), (c) 1,1'-carbonyl-bis-(2-methylimidazole), (d) 1,1'-carbonyl-dipiperidine, (e) N,N'-dicyclohexylcarbodiimide (DCC), (f) N,N"-diisopropylcarbodiimide (DIC), (g) 1-ethyl-3-(3-dimethylaminopropyl)carbodiimide (EDC) and a combination of one of the previous with (h) N-hydroxysuccinimide or (i) N-hydroxyphthalimide in an adequate solvent, and, optionally
ii) isolation of the compound of formula (IV).

The compounds of formula (IV) allow obtaining Roflumilast by a process including, as main advantage, the use of bases alternative to sodium hydride or tert-BuOK, that are much more advisable in a industrial process, where it is not necessary to use a high excess of 3,5-dichloropyridine-4-amine. In fact, this process can work adequately with 1-1.5 equivalents of 3,5-dichloropyridine-4-amine for each acid equivalent, which involves cost savings in the process and an environmental improvement. All these characteristics provide safety, environmental and economic advantages over the procedures known in the state of the art.

Therefore, an additional embodiment of this invention is aimed at the use of compounds of formula (IV) for obtaining Roflumilast.

Another additional embodiment of the invention is aimed at a process for obtaining Roflumilast that comprises the preparation of a compound of formula (IV), as previously described, and the subsequent reaction of the compound of formula (IV) with 3,5-dichloropyridine-4-amine, compound of formula (III):

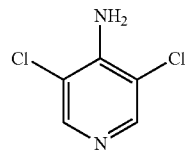
(III)

in the presence of an inorganic base selected among alkaline hydroxides, alkaline carbonates and alkaline fluorides, in an adequate solvent, and, optionally, in the presence of a drying agent.

An additional embodiment of this invention relates to an intermediate compound of formula (IV):

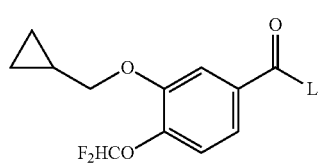
(IV)

where L is selected from (a) 1H-imidazol-1-yl, (b) 1H-1,2,4-triazol-1-yl, (c) 2-methyl-1H-imidazole-1-yl, (d) piperidin-1-yl, (h) 2,5-dioxopyrrolidin-1-yloxy and (i) 1,3-dioxoisoindolin-2-yloxy,

BRIEF DESCRIPTION OF THE FIGURES

FIG. 1. shows the X-ray powder diffraction diagram for the Roflumilast obtained by the process of this invention. The intensity, in the y-axis, is expressed in a counting linear scale. The abscissa corresponds to the angle 2θ°.

DETAILED DESCRIPTION OF THE INVENTION

The process for obtaining the compound of formula (IV) responds to the following scheme (I):

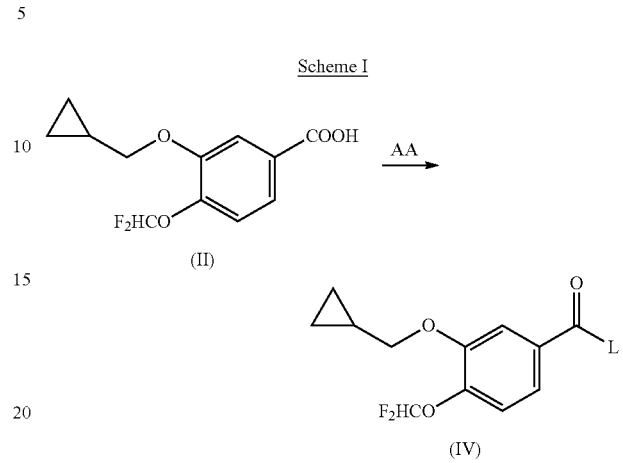

where:

AA means an activating agent selected from (a) carbonyldiimidazole (CD), (b) 1,1'-carbonyl-di-(1,2,4-triazol) (CDT), (c) 1,1'-carbonyl-bis-(2-methylimidazole), (d) 1,1'-carbonyldipiperidin, (e) N,N'-dicyclohexylcarbodiimide (DCC), (f) N,N'-diisopropylcarbodiimide (DIC), (g) 1-ethyl-3-(3-dimethylaminopropyl)carbodiimide (EDC) and a combination of one of the previous (a)-(g) with (h) N-hydroxysuccinimide or (i) N-hydroxyphthalimide;

L means respectively (a) 1H-imidazol-1-yl, (b) 1H-1,2,4-triazol-1-yl, (c) 2-methyl-1H-imidazol-1-yl, (d) piperidin-1-yl, (e) N,N'-dicyclohexylcarbamimidoyloxy, (f) N,N'-diisopropylcarbamimidoyloxy, (g) N'-(3-(dimethylamino)propyl)-N-ethylcarbamimidoyloxy, (h) 2,5-dioxopyrrolidin-1-yloxy and (i) 1,3-dioxoisoindolin-2-yloxy.

Table 1 shows the meaning of the activating agents AA and of the corresponding L groups.

TABLE 1

| | AA activating agent | | Group L | |
|---|---|---|---|---|
| a) | carbonyldiimidazole (CDI) | | 1H-imidazol-1-yl | |
| b) | 1,1'-carbonyl-di-(1,2,4-triazol) (CDT) | | 1H-1,2,4-triazol-1-yl | |
| c) | 1,1'-carbonyl-bis-(2-methylimidazole) | | 2-methyl-1H-imidazol-1-yl | |

TABLE 1-continued

| | AA activating agent | | Group L | |
|---|---|---|---|---|
| d) | 1,1'-carbonyl-dipiperidine | 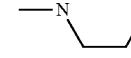 | piperidine-1-yl | 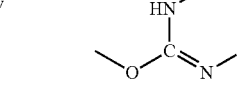 |
| e) | N,N'-dicyclohexyl carbodiimide (DCC) | | N,N'-dicyclohexyl carbamimidoyloxy | |
| f) | N,N'-diisopropyl carbodiimide (DIC) | | N,N'-diisopropyl carbamimidoyloxy | |
| g) | 1-ethyl-3-(3-dimethylaminopropyl) carbodiimide (EDC) | | N'-(3-(dimethylamine)propyl)-N-ethyl carbamimidoylox | |
| h) | N-hidroxysuccinimide | | 2,5-dioxopyrrolidin-1-yloxy | |
| i) | N-hydroxyphthalamide | | 1,3-dioxoisoindolin-2-yloxy | |

In a preferred embodiment, the activating agent is selected from (a) carbonyldiimidazole (CDI), (b) 1,1'-carbonyl-di-(1,2,4-triazol) (CDT), (c) 1,1'-carbonyl-bis-(2-methylimidazole), (d) 1,1'-carbonyl-dipiperidin, and a combination of one of the previous (a)-(d) with (h) N-hydroxysuccinimide or (i) N-hydroxyphthalimide; More preferably, the activating agent is selected from (a) carbonyldiimidazole (CDI), (b) 1,1'-carbonyl-di-(1,2,4-triazol) (CDT) and (c) 1,1'-carbonyl-bis-(2-methylimidazole). In a more preferred embodiment, the activating agent is (a) carbonyldiimidazole (CDI) or (b) 1,1'-carbonyl-di-(1,2,4-triazol) (CDT), and the resulting activated intermediate is the compound of formula (IV) where L is (a) 1H-imidazol-1-yl (IVa) or (b) 1H-1,2,4-triazol-1-yl (IVb) respectively.

In another preferred embodiment, the solvent of step (i) is selected from dimethylsulphoxide, dimethylformamide, dymethylacetamide, tetrahydrofuran, methyl-tetrahydrofuran, acetone, methyl ethyl ketone, methyl isobutyl ketone, dichloromethane, and mixtures thereof.

In a more preferred embodiment, the solvent of step (i) is selected from tetrahydrofuran, dimethylsulphoxide, and mixtures thereof.

In an even more preferred embodiment, the solvent of step (i) is dimethylsulphoxide.

Optionally, the compound of formula (IV) can be isolated by conventional methods known by a person skilled in the art.

The starting compounds of formula (II) can be prepared from methods known by a person skilled in the art, such as those described in the documents of the state of the art mentioned in the background of this invention. Examples 1 and 2 set out in this document describe also a procedure for obtaining it.

The compounds of formula (IV) can be used as reagents for the preparation of Roflumilast as described above.

Therefore, an additional aspect of this invention relates to a process for obtaining Roflumilast that comprises:

i) activation of a compound of formula (II):

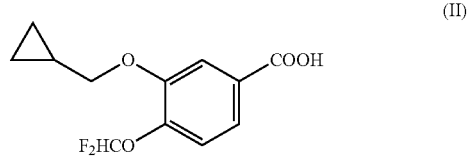

(II)

with an activating agent selected from (a) carbonyldiimidazole (CD), (b) 1,1'-carbonyl-di-(1,2,4-triazol) (CDT), (c) 1,1'-carbonyl-bis-(2-methylimidazole), (d) 1,1'-carbonyl-dipiperidin, (e) N,N'-dicyclohexylcarbodiimide (DCC), (f) N,N'-diisopropylcarbodiimide (DIC), (g) 1-ethyl-3-(3-dimethylaminopropyl)carbodiimide (EDC) and a combination of one of the previous with (h) N-hydroxysuccinimide or (i) N-hydroxyphthalimide in an adequate solvent, to give an activated compound of (II), of general formula (IV):

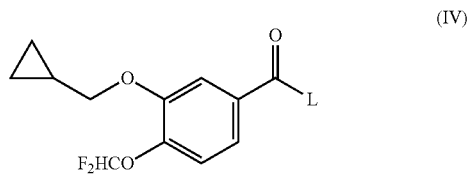

(IV)

where L is, respectively, (a) 1H-imidazol-1-yl, (b) 1H-1,2,4-triazol-1-yl, (c) 2-methyl-1H-imidazole-1-yl, (d) piperidin-1-yl, (e) N,N'-dicyclohexylcarbamimidoyloxi, (f) N,N'-diisopropylcarbamimidoyloxi, (g) N'-(3-(dimethylamino)propyl)-N-ethylcarbamimidoyloxy, (h) 2,5-dioxopyrrolidin-1-yloxy or (i) 1,3-dioxoisoindolin-2-yloxy;

ii) optionally, isolation of the compound of formula (IV); and iii) reaction of the compound of formula (IV) with 3,5-dichloropyridine-4-amine, in the presence of an inorganic basic selected among alkaline hydroxides, alkaline carbonates and alkaline fluorides, in an adequate solvent, and, optionally, in the presence of a drying agent.

This process has the following scheme (II):

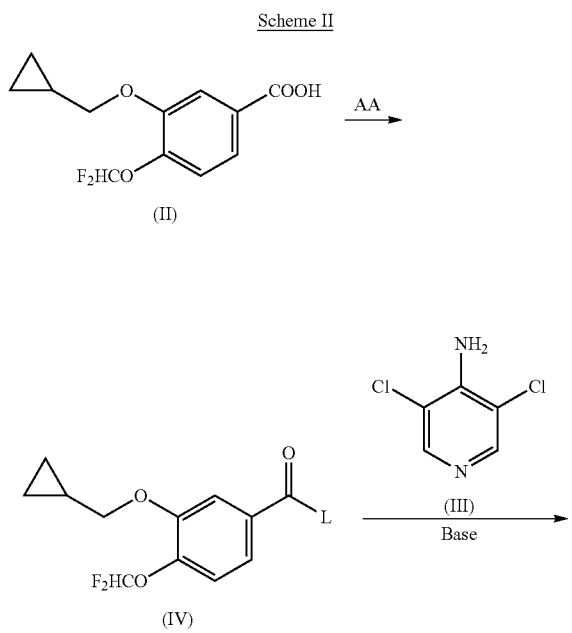

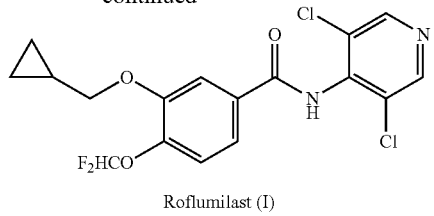

Roflumilast (I)

where AA and L are defined as above.

In a preferred embodiment, the activating agent is selected from (a) carbonyldiimidazole (CDI), (b) 1,1'-carbonyl-di-(1,2,4-triazol) (CDT), (c) 1,1'-carbonyl-bis-(2-methylimidazole), (d) 1,1'-carbonyl-dipiperidin, and a combination of one of the previous with (a)-(d) with (h) N-hydroxysuccinimide or (i) N-hydroxyphthalimide. More preferably, the activating agent is selected from (a) carbonyldiimidazole (CDI), (b) 1,1'-carbonyl-di-(1,2,4-triazol) (CDT) and (c) 1,1'-carbonyl-bis-(2-methylimidazole). In a more preferred embodiment, the activating agent is (a) carbonyldiimidazole (CDI) or (b) 1,1'-carbonyl-di-(1,2,4-triazol) (CDT), and the resulting activated intermediate is the compound of formula (IV) where L is (a) 1H-imidazol-1-yl (IVa) or (b) 1H-1,2,4-triazol-1-yl (IVb) respectively.

In another preferred embodiment, the solvent of step (i) is selected from dimethylsulphoxide, dimethylformamide, dimethylacetamide, tetrahydrofuran, methyl-tetrahydrofuran, acetone, methyl ethyl ketone, methyl isobutyl ketone, dichloromethane, and mixtures thereof.

In a more preferred embodiment, the solvent of step (i) is selected from tetrahydrofuran, dimethylsulphoxide and mixtures thereof.

In an even more preferred embodiment, the solvent of step (i) is dimethylsulphoxide.

Optionally, the compound of formula (IV) can be isolated by conventional methods known by a person skilled in the art.

In a preferred embodiment, the percentage of the compound of formula (III) is 1-1.5 equivalents with respect to the compound of formula (II).

In another preferred embodiment, in step (iii) alkaline hydroxides are selected from lithium hydroxide, sodium hydroxide, potassium hydroxide, and caesium hydroxide.

In another preferred embodiment, alkaline carbonates are selected from potassium carbonate and caesium carbonate.

In another preferred embodiment, alkaline fluoride is caesium fluoride.

In another preferred embodiment, the inorganic base of step (iii) is sodium hydroxide or caesium carbonate, in the presence of a drying agent, or caesium fluoride. More preferably, the inorganic base is caesium fluoride.

In another preferred embodiment, the molar ratio of the inorganic base of step (iii) to 3-(cyclopropylmethoxy)-4-(difluoromethoxy)-benzoic acid (II) is 1.2-3 and preferably 2.4-2.8 base equivalents with respect to (II).

In another preferred embodiment, the solvent of step (i) is selected from dimethylsulphoxide, dimethylformamide, dimethylacetamide, tetrahydrofuran, methyl-tetrahydrofuran, acetone, methyl ethyl ketone, methyl isobutyl ketone, dichloromethane, and mixtures thereof. More preferably the solvent of step (iii) is dimethylsulphoxide.

In another preferred embodiment, when the presence of a drying agent is necessary, it is selected from magnesium sulphate and sodium sulphate.

In another preferred embodiment, the inorganic base is caesium fluoride and the solvent is dimethylsulphoxide (DMSO), thus avoiding the use of dimethylformamide, a more toxic solvent than DMSO.

Another object of this invention is a compound of general formula (IV):

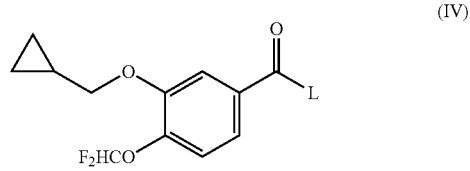

(IV)

where L is (a) 1H-imidazol-1-yl, (b) 1H-1,2,4-triazol-1-yl, (c) 2-methyl-1H-imidazol-1-yl, (d) piperidin-1-yl, (h) 2,5-dioxopyrrolidin-1-yloxy or (i) 1,3-dioxoisoindolin-2-yloxy.

More preferably, the compounds of general formula (IV) are also object of this invention, where L is (a) 1H-imidazol-1-yl, of formula (IVa)

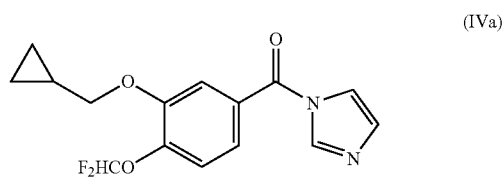

(IVa)

or L is (b) 1H-1,2,4-triazol-1-yl, of formula (IVb)

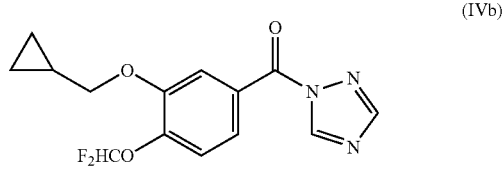 [SMILES: O=C(c1ccc(OC(F)F)c(OCC2CC2)c1)n1cncn1]

(IVb)

This invention is illustrated additionally by the following examples, that do not intend to limit its scope.

EXAMPLES

Example 1

Preparation of 3-(cyclopropylmethoxy)-4-(difluoromethoxy)-benzaldehyde 55 g of 4-(difluoromethoxy)-3-hydroxybenzaldehyde, 42.42 g of $K_2CO_3$ (1.05 eq), 4.86 g of KI (0.1 eq) and 220 mL of dimethylsulphoxide (DMSO) were loaded in a reactor. The mixture was heated at 70° C. and kept for 1 h. A mixture previously prepared of 42.65 g of bromomethyl cyclopropane (1.08 eq) and 110 mL of DMSO was added for 1 hour. The reaction was kept for 3 h at 70° C., and then cooled at room temperature. Once the temperature was reached, 375 mL of toluene was added. The suspension was filtered to remove the remaining $K_2CO_3$, and then it was cooled at 0-5° C., and 375 mL of deionised water were loaded. The phases were separated and the organic phase was washed twice with 55 mL of deionised water. The solvent was removed at reduced pressure, obtaining 70 g (yield 99%) of 3-(cyclopropylmethoxy)-4-(difluoromethoxy)-benzaldehyde as a viscous yellowish fluid.

Example 2

Preparation of 3-(cyclopropylmethoxy)-4-(difluoromethoxy)-benzoic acid (II)

40 g of 3-(cyclopropylmethoxy)-4-(difluoromethoxy)-benzaldehyde 160 mL of glacial acetic acid and 32.0 g of sulphamic acid (2.0 eq) were loaded in a reactor. The mixture was cooled at 5-10° C. and the temperature was not allowed to exceed 20° C., adding slowly a previously prepared solution of 44.77 g of sodium chloride and 61 mL of deionised water. After the addition, the reaction was kept for 1 hour at 15-20° C. 450 mL of deionised water was loaded and then it was cooled at 0-5° C. and kept for 1 h at this temperature. The solid was filtered and washed four times with 200 mL of deionised water. The product was dried for 15 h at 40° C., obtaining 36 g (yield 85%) of 3-(cyclopropylmethoxy)-4-(difluoromethoxy)-benzoic acid (II) as solid.

Example 3

Preparation of Roflumilast (I)

Preparation of (3-(cyclopropylmethoxy)-4-(difluoromethoxy)-phenyl)(1H-imidazol-1-yl)-methanone (IVa)

50 mL of tetrahydrofuran (THF) were added to 5.0 g of 3-(cyclopropylmethoxy)-4-(difluoromethoxy)-benzoic acid (II) and 3.46 g of CDI (1.1 eq). The mixture was stirred for 2 h at room temperature. Then, the THF was removed by distillation, obtaining (3-(cyclopropylmethoxy)-4-(difluoromethoxy)-phenyl)(1H-imidazol-1-yl)-methanone (IVa) as viscous oil.

$^1$H-RMN (DMSO-$D_6$): 8.07 (s, 1H), 7.86 (s, 1H), 7.64-7.57 (m, 2H), 7.27-7.12 (m, 2H), 7.12 (s, 1H), 3.95-3.92 (d, 2H, J=12 Hz), 1.30-1.19, (m, 1H), 0.60-0.34 (dm, 4H).

$^{13}$C-RMN (DMSO-$D_6$): 167.44 (C), 149.53 (C), 143.12 (C), 135.27 (CH), 130.59 (C), 122.38 (CH), 121.57 (CH), 120.31 (CH), 116.68 (CH), 114.99 (CH), 112.58 (CH), 73.28 ($CH_2$), 10.11 ($CH_2$), 3.18 (CH).

Formation of Roflumilast 60 mL of DMSO were added to 3.79 g of 3,5-dichloropyridin-4-amine (III) (1.2 eq) and 0.891 g of NaOH (1.15 eq). The mixture was stirred at a temperature of 50° C. for 2 h. A suspension was obtained to which 7.426 g of anhydrous $Na_2SO_4$ were added as drying agent.

(3-(cyclopropylmethoxy)-4-(difluoromethoxy)-phenyl) (1H-imidazol-1-yl)-methanone (IVa) is dissolved in 40 mL of DMSO and this solution is slowly added over the previous mixture for 30 min at a temperature of 25-30° C. The reaction was allowed to react at this temperature for 16 h. Once the reaction was completed, 150 mL of water were added and the pH was adjusted to pH=7.0 with 1 N HCl. Product precipitation was seen and isolated by filtration. The filtered solid was washed consecutively with 100 mL of 5% $NaHCO_3$, 100 mL of 0.01 N HCl 0.01N and 100 mL of $H_2O$. The washed solid was dried in a vacuum oven for 14 h at 50° C. 5.44 g of raw product were obtained and recrystallised with a mixture of isopropanol-water at 90%. The recrystallised solid was dried in a vacuum oven at 50° C. 4.90 g of Roflumilast were obtained (yield 63%).

X-ray (angle values 2-theta (θ)): 5.5; 12.3; 16.1; 16.6; 18.1; 22.4; 22.6; 24.1; 24.4; 24.7 and 26.9 measured in an X-ray diffractometer with radiation Cu Kα (1,5406 Å) (FIG. 1).

Example 4

Preparation of Roflumilast (I)

Preparation of (3-(cyclopropylmethoxy)-4-(difluoromethoxy)-phenyl)(1H-imidazol-1-yl)-methanone (IVa)

30 mL of DMSO were added to 10.0 g of 3-(cyclopropylmethoxy)-4-(difluoromethoxy)-benzoic acid (II) and 7.54 g of CDI (1.2 eq). The mixture was stirred for 3 h at room temperature. Then, THF was removed by distillation and replaced by 40 mL of DMSO. A solution of (3-(cyclopropylmethoxy)-4-(difluoromethoxy)-phenyl)(1H-imidazol-1-yl)-methanone (IVa) in DMSO was thus obtained.

Formation of Roflumilast 50 mL of DMSO were added to 7.58 g of 3,5-dichloropyridin-4-amine (III) (1.2 eq) and 16.47 g of CsF (2.8 eq). The mixture was stirred at a temperature of 90° C. for 3 h. A suspension was obtained.

A solution in DMSO of (3-(cyclopropylmethoxy)-4-(difluoromethoxy)-phenyl)(1H-imidazol-1-yl)-methanone (IVa) was slowly loaded over the previous suspension for 30 min at a temperature of 90-95° C. The reaction was allowed to react at this temperature for 6 h. Once the reaction was completed, 100 mL of water were added and the pH was adjusted to pH=5.0 with 1 N HCl. Product precipitation was seen and isolated by filtration. The filtered solid was washed with 100 mL of $H_2O$. The washed solid was dried in a vacuum oven for 14 h at 50° C. 15.3 g of raw product were obtained and recrystallised with a mixture of isopropanol-water at 90%. The recrystallised solid was dried in a vacuum oven at 50° C. 13.90 g of roflumilast were obtained (yield 88%).

The X-ray diffraction diagram is consistent with that of Example 3.

Example 5

Preparation of Roflumilast (I)

Preparation of (3-(cyclopropylmethoxy)-4-(difluoromethoxy)-phenyl)(1H-imidazol-1-yl)-methanone (IVa)

30 mL of THF were added to 5.0 g of 3-(cyclopropylmethoxy)-4-(difluoromethoxy)-benzoic acid (II) and 3.77 g of CDI (1.2 eq). The mixture was stirred for 2 h at room temperature. Then, THF was removed by distillation and replaced by 30 mL of DMSO. A solution of (3-(cyclopropylmethoxy)-4-(difluoromethoxy)-phenyl)(1H-imidazol-1-yl)-methanone (IVa) in DMSO was thus obtained.

Formation of Roflumilast 50 mL of DMSO were added to 4.42 g of 3,5-dichloropyridin-4-amine (III) (1.4 eq) and 15.14 g of $Cs_2CO_3$ (2.4 eq). The mixture was stirred at a temperature of 90° C. for 3 h. A suspension was obtained.

A solution in DMSO of (3-(cyclopropylmethoxy)-4-(difluoromethoxy)-phenyl)(1H-imidazol-1-yl)-methanone (IVa) was slowly added to 30 min. over the previous suspension at a temperature of 90-95° C. The reaction was allowed to react at this temperature for 6 h. Once the reaction was completed, 75 mL of water were added and the pH was adjusted to pH=2.0 with 1 N HCl. Product precipitation was seen and isolated by filtration. The filtered solid was washed with 100 mL of $H_2O$. The washed solid was dried in a vacuum oven for 14 h at 50° C. 5.94 g of raw product were obtained and recrystallised with a mixture of isopropanol-water at 90%. The recrystallised solid was dried in a vacuum oven at 50° C. 5.35 g of Roflumilast were obtained (yield 68%).

The X-ray diffraction diagram is consistent with that of Example 3.

Example 6

Preparation of Roflumilast (I)

Preparation of (3-(cyclopropylmethoxy)-4-(difluoromethoxy)-phenyl)(1H-1,2,4-triazol-1-yl)-methanone (IVb)

15 mL of DMSO were added to 5.0 g of 3-(cyclopropylmethoxy)-4-(difluoromethoxy)-benzoic acid (II) and 3.81 g of CDT (1.2 eq). The mixture was stirred for 2 h at room temperature. A solution of (3-(cyclopropylmethoxy)-4-(difluoromethoxy)-phenyl)(1H-1,2,4-triazol-1-yl)-methanone (IVb) in DMSO was thus obtained.

Formation of Roflumilast 25 mL of DMSO were added to 3.79 g of 3,5-dichloropyridin-4-amine (III) (1.2 eq) and 8.23 g of CsF (2.8 eq). The mixture was stirred at a temperature of 90° C. for 3 h. A suspension was obtained.

A solution of (3-(cyclopropylmethoxy)-4-(difluoromethoxy)-phenyl)(1H-1,2,4-triazol-1-yl)-methanone (IVb) in DMSO was slowly loaded over the previous suspension in DMSO at a temperature of 90-95° C. The reaction was allowed to react at this temperature for 3 h. Once the reaction was completed, 50 mL of water were added and the pH was adjusted to pH=4.5 with 1 N HCl. Product precipitation was seen and isolated by filtration. The filtered solid was washed with 100 mL of $H_2O$. The washed solid was dried in a vacuum oven for 14 h at 50° C. 6.55 g of raw product were obtained and recrystallised with a mixture of isopropanol-water at 90%. The recrystallised solid was dried in a vacuum oven at 50° C. 6.15 g of Roflumilast were obtained (yield 79%).

The X-ray diffraction diagram is consistent with that of Example 3.

Example 7

Preparation of roflumilast (I)

Preparation of (3-(cyclopropylmethoxy)-4-(difluoromethoxy)-phenyl)(1H-imidazol-1-yl)-methanone (IVa)

32 mL of DMSO were added to 4.0 g of 3-(cyclopropylmethoxy)-4-(difluoromethoxy)-benzoic acid (II) and 3.02 g of CDI (1.2 eq). The mixture was stirred for 2 hours at room temperature. A solution of (3-(cyclopropylmethoxy)-4-(difluoromethoxy)-phenyl)(1H-imidazol-1-yl)-methanone (IVa) in DMSO was obtained.

Formation of Roflumilast:

2.78 g of 3,5-dichloropyridin-4-amine (III) and 6.59 g of CsF were loaded over a solution of (3-(cyclopropylmethoxy)-4-(difluoromethoxy)-phenyl)(1H-imidazol-1-yl)-methanone (IVa) in DMSO, at room temperature. The mixture was heated at 90° C. and left at this temperature for 6 h. After the reaction was completed, 100 mL of water were added and the pH was adjusted to 6.0 with 1 N HCl. Product precipitation was seen and isolated by filtration. The filtered solid was washed with 100 mL of $H_2O$. The washed solid was dried in a vacuum oven for 14 h at 50° C.

5.30 g of raw product were obtained and recrystallised with a mixture of isopropanol-water 90%. The recrystallised solid was dried in a vacuum oven at 50° C. 4.35 g of Roflumilast were obtained (yield 70%).

The X-ray diffraction diagram is consistent with that of Example 3.

The invention claimed is:

1. A process for preparing a compound of formula (IV):

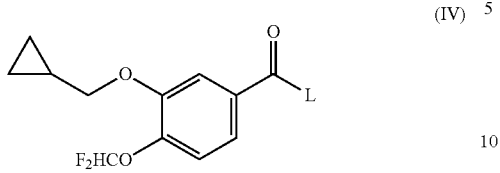

where L is (a) 1H-imidazol-1-yl, (b) 1H-1,2,4-triazol-1-yl, (c) 2-methyl-1H-imidazol-1-yl, (d) piperidin-1-yl, (e) N,N'-dicyclohexylcarbamimidoyloxy, (f) N,N'-diisopropylcarbamimidoyloxy, (g) N'-(3-(dimethylamino)propyl)-N-ethylcarbamimidoyloxy, (h) 2,5-dioxopyrrolidin-1-yloxy, or (i) 1,3-dioxoisoindolin-2-yloxy, comprising:
i) activation of a compound of formula (II):

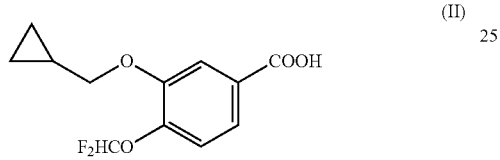

with an activating agent selected, respectively, from (a) carbonyldiimidazole (CDI), (b) 1,1'-carbonyl-di-(1,2,4-triazol) (CDT), (c) 1,1'-carbonyl-bis-(2-methylimidazole), (d) 1,1'-carbonyl-dipiperidin, (e) N,N'-dicyclohexylcarbodiimide (DCC), (f) N,N'-diisopropylcarbodiimide (DIC), (g) 1-ethyl-3-(3-dimethylaminopropyl)carbodiimide (EDC) and a combination of one of the previous with (h) N-hydroxysuccinimide or (i) N-hydroxyphthalimide in an adequate solvent, and, optionally
ii) isolation of the compound of formula (IV).

2. The process according to claim 1, wherein the activating agent is selected from (a) carbonyldiimidazole (CDI), (b) 1,1'-carbonyl-di-(1,2,4-triazol) (CDT) and (c) 1,1'-carbonyl-bis-(2-methylimidazole).

3. The process according to claim 1, wherein the activating agent is (a) carbonyldiimidazole (CDI).

4. The process according to claim 1, wherein the activating agent is (b) 1,1'-carbonyl-di-(1,2,4-triazol) (CDT).

5. The process according to claim 1, wherein the solvent of step
(i) is selected from dimethylsulphoxide, dimethylformamide, dimethylacetamide, tetrahydrofuran, methyl-tetrahydrofuran, acetone, methyl ethyl ketone, methyl isobutyl ketone, dichloromethane, and mixtures thereof.

6. The process according to claim 1, wherein the solvent of step
(i) is selected from tetrahydrofuran, dimethylsulphoxide and mixtures thereof.

7. The process according to claim 1, wherein the solvent of step
(i) is dimethylsulphoxide.

8. A Process for the preparation of Roflumilast (I):

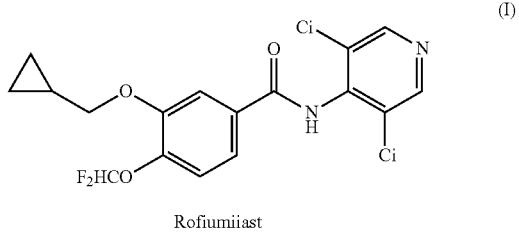

Roflumilast comprising:
i) activation of a compound of formula (II):

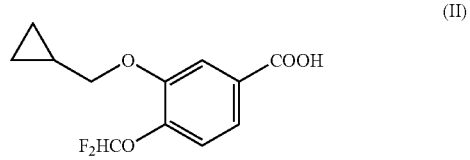 [SMILES: O=C(O)c1ccc(OC(F)F)c(OCC2CC2)c1]

with an activating agent selected from (a) carbonyldiimidazole (CDI), (b) 1,1'-carbonyl-di-(1,2,4-triazol) (CDT), (c) 1,1'-carbonyl-bis-(2-methylmidazole), (d) 1,1'-carbonyl-dipiperidin, (e) N,N'-dicyclohexylcarbodiimide (DCC), (f) N,N'-diisopropylcarbodiimide (DIC), (g) 1-ethyl-3-(3-dimethylaminopropyl)carbodiimide (EDC) and a combination of one of the previous with (h) N-hydroxysuccinimide or (i) N-hydroxyphthalimide in an adequate solvent, to give an activated compound of (II), of formula (IV):

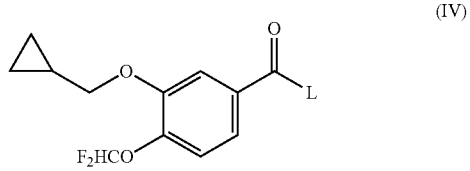

where L is, respectively, (a) 1H-imidazol-1-yl, (b) 1H-1,2,4-triazol-1-yl, (c) 2-methyl-1H-imidazole-1-yil, (d) piperidin-1-yl, (e) N,N'-dicyclohexylcarbamimidoyloxi, (f) N,N'-diisopropylcarbamimidoyloxi, (g) N'-(3-(dimethylamino)propyl)-N-ethylcarbamimidoyloxy, (h) 2,5-dioxopyrrolidin-1-yloxy or (i) 1,3-dioxoisoindolin-2-yloxy;
ii) optionally, isolation of the compound of formula (IV); and
iii) reaction of the compound of formula (IV) with 3,5-dichloropyridin-4-amine of formula (III),

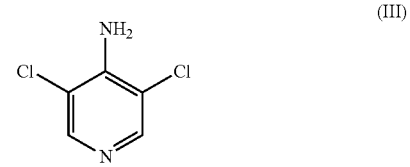

in the presence of an inorganic base selected among alkali hydroxides, alkali carbonates and alkali fluorides, in an adequate solvent, and, optionally, in the presence of a drying agent,
wherein steps (i) and (ii) are defined as in claim 1.

9. The process according to claim 8, wherein the proportion of the compound of formula (III) ranges from 1 to 1.5 equivalents with respect to the compound of formula (II).

10. The process according to claim 8, wherein the alkali hydroxides are selected from lithium hydroxide, sodium hydroxide, potassium hydroxide and caesium hydroxide.

11. The process according to claim 8, wherein the alkali carbonates are selected from potassium carbonate and caesium carbonate.

12. The process according to claim 8, wherein the alkali fluoride is caesium fluoride.

13. The process according to claim 8, wherein the inorganic base is sodium hydroxide or caesium carbonate, in the presence of a drying agent, or caesium fluoride.

14. The process according to claim 8, wherein the inorganic base is caesium fluoride.

15. The process according to claim 8, wherein the solvent in step (iii) is selected from dimethylsulphoxide, dimethylformamide, dimethylacetamide, tetrahydrofuran, methyl-tetrahydrofuran, acetone, methyl ethyl ketone, methyl isobutyl ketone, dichloromethane, and mixtures thereof.

16. The process according to claim 15, wherein the solvent is dimethylsulphoxide.

17. The process according to claim 8, wherein the drying agent is selected from magnesium sulphate and sodium sulphate.

18. A compound of formula (IV):

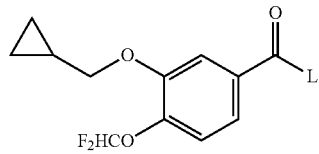

(IV)

where L is (a) 1H-imidazol-1-yl, (b) 1H-1,2,4-triazol-1-yl, (c) 2-methyl-1H-imidazol-1-yl, (d) piperidin-1-yl, (h) 2,5-dioxopyrrolidin-1-yloxy or (i) 1,3-dioxoisoindolin-2-yloxy.

19. The compound according to claim 18, wherein L is (a) 1H-imidazol-1-yl, of formula (IVa):

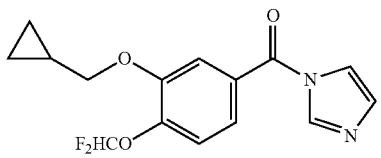

(IVa)

20. The compound according to claim 18, wherein L is (a) 1H-1,2,4-triazol-1-yl, of formula (IVb):

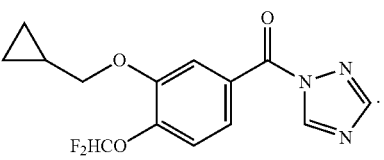

(IVb)

* * * * *